US012571806B2

(12) United States Patent
Satoh et al.

(10) Patent No.: US 12,571,806 B2
(45) Date of Patent: Mar. 10, 2026

(54) METHOD FOR ASSISTING DETECTION OF NON-ALCOHOLIC STEATOHEPATITIS

(71) Applicants:Denka Company Limited, Tokyo (JP); NATIONAL UNIVERSITY CORPORATION HOKKAIDO UNIVERSITY, Sapporo (JP); NATIONAL UNIVERSITY CORPORATION OKAYAMA UNIVERSITY, Okayama (JP)

(72) Inventors: Noriyuki Satoh, Gosen (JP); Yasuki Ito, Tokyo (JP); Toshihiro Sakurai, Sapporo (JP); Masahiro Mizuta, Sapporo (JP); Shu-Ping Hui, Sapporo (JP); Kazuhiro Nouso, Okayama (JP); Hiroyuki Okada, Okayama (JP)

(73) Assignees: DENKA COMPANY LIMITED, Tokyo (JP); NATIONAL UNIVERSITY CORPORATION HOKKAIDO UNIVERSITY, Sapporo (JP); NATIONAL UNIVERSITY CORPORATION OKAYAMA UNIVERSITY, Okayama (JP)

( * ) Notice: Subject to any disclaimer, the term of this patent is extended or adjusted under 35 U.S.C. 154(b) by 739 days.

(21) Appl. No.: 17/797,284

(22) PCT Filed: Feb. 4, 2021

(86) PCT No.: PCT/JP2021/004008
§ 371 (c)(1),
(2) Date: Aug. 3, 2022

(87) PCT Pub. No.: WO2021/157631
PCT Pub. Date: Aug. 12, 2021

(65) Prior Publication Data
US 2023/0060781 A1 Mar. 2, 2023

(30) Foreign Application Priority Data

Feb. 4, 2020 (JP) ................................. 2020-016820

(51) Int. Cl.
*G01N 33/92* (2006.01)
*C12Q 1/60* (2006.01)

(52) U.S. Cl.
CPC ............... *G01N 33/92* (2013.01); *C12Q 1/60* (2013.01)

(58) Field of Classification Search
None
See application file for complete search history.

(56) References Cited

U.S. PATENT DOCUMENTS

2013/0253174 A1 9/2013 Chiba et al.

FOREIGN PATENT DOCUMENTS

EP 3 842 805 A1 6/2021
JP 2010-94131 A 4/2010
(Continued)

OTHER PUBLICATIONS

Ito, Y et al. Development and population results of a fully automated homogeneous assay for LDL triglyceride. J Appl. Lab. Med. 2018. 2(5): 746-756. (Year: 2018).*
(Continued)

*Primary Examiner* — Xiaoyun R Xu
(74) *Attorney, Agent, or Firm* — Birch, Stewart, Kolasch & Birch, LLP

(57) ABSTRACT

Provided is a method of assisting the detection of nonalcoholic steatohepatitis (NASH), which is far less invasive than liver biopsy and is based on simple operations that do not require skilled technical personnel.
The present invention is a method of assisting the detection of NASH, which includes:
(Continued)

a) measuring the amount of LDL-TG contained in a test blood sample isolated from a living body;

b) measuring the amount of at least one component selected from the group consisting of LDL-C, LDL subfraction-C, IIDL-C, HDL subfraction-C, ApoB, ApoE, total cholesterol, ALT, and AST contained in the test blood sample; and c) determining the possibility of developing and/or having NASH by using the amount of LDL-TG in combination with the amount of the at least one component.

8 Claims, 1 Drawing Sheet

(56) References Cited

FOREIGN PATENT DOCUMENTS

| JP | 2018-508774 A | 3/2018 |
| JP | 2018-80943 A | 5/2018 |
| WO | WO 2005/108006 A1 | 11/2005 |
| WO | WO 2011/136332 A1 | 11/2011 |
| WO | WO 2011/158769 A1 | 12/2011 |
| WO | WO 2012/105590 A1 | 8/2012 |
| WO | WO 2019/175962 A1 | 9/2019 |

OTHER PUBLICATIONS

Extended European Search Report for European Application No. 21750163.4, dated May 31, 2023.

Fuji et al., "Low-Density Lipoprotein (LDL)-Triglyceride and Its Ratio to LDL-Cholesterol as Diagnostic Biomarkers for Nonalcoholic Steatohepatitis", The Journal of Applied Laboratory Medicine, vol. 5, No. 6. Nov. 2020, pp. 1206-1215.

Fujii et al. "Low-Density Lipoprotein (LDL)—Triglyceride and Its Ratio to LDL-Cholesterol as Diagnostic Biomarkers for Nonalcoholic Steatohepatitis", The Journal of Applied Laboratory Medicine, May 1, 2020, vol. 5, No. 6, p. 1206-1215.

International Search Report for International Application No. PCT/JP2021/004008, dated Apr. 6, 2021, with English translation.

* cited by examiner

METHOD FOR ASSISTING DETECTION OF NON-ALCOHOLIC STEATOHEPATITIS

TECHNICAL FIELD

The present invention relates to a method of assisting the detection of nonalcoholic steatohepatitis.

BACKGROUND ART

Nonalcoholic fatty liver disease (hereinafter also referred to as "NAFLD") refers to medical conditions characterized by steatosis, which is confirmed by histological examination or diagnostic imaging, except for liver diseases such as viral hepatitis, autoimmune hepatitis, and alcoholic liver disease, and the prevalence of this disease is rapidly increasing worldwide in association with an increasing number of people who suffer from obesity. NAFLD is classified into nonalcoholic fatty liver (hereinafter also referred to as "NAFL"), which is thought to rarely progress, and nonalcoholic steatohepatitis (hereinafter also referred to as "NASH"), which is progressive and causes liver cirrhosis and liver cancer. Characteristic pathological features of NASH include fatty degeneration, ballooning degeneration, inflammation, and fibrosis.

A definitive diagnosis based on liver biopsy is needed to discriminate various disease states in the liver, including fatty degeneration, and to distinguish between NAFL and NASH. However, liver biopsy is an invasive and expensive examination, and therefore causes patients to feel exhausted in different ways. Additionally, the skills of practicing technicians may affect the liver biopsy, as exemplified by sampling errors that occur at a certain probability, and the same is true for examination of collected samples. Thus, patients need to visit specific institutions to receive a certain level of medical care, which has, problematically, increased burden on patients.

Meanwhile, examples of laboratory test items that are commonly carried out in relation to liver diseases include aspartate aminotransferase (AST), alanine aminotransferase (ALT), AST/ALT ratio, and the like; markers for inflammation and cytokine, such as TNF-α, high-sensitivity CRP, and ferritin; cytokeratin 18 fragments as apoptosis markers; and fibrosis markers, such as hyaluronic acid and type IV collagen 7S (Patent Documents 1 and 2). However, there have not been established biomarkers for predicting the presence of NASH, which are detected in people who suffer from a plurality of medical conditions associated with NASH. That is, there have been found no biomarkers that comprehensively reflect the pathological characteristics associated with NASH.

PRIOR ART DOCUMENTS

Patent Documents

Patent Document 1: JP 2010-94131 A
Patent Document 2: JP 2018-80943 A

SUMMARY OF THE INVENTION

Problems to be Solved by the Invention

An object of the present invention is to provide a method of assisting the detection of NASI I, which is far less invasive than liver biopsy and is based on a series of simple operations that do not require skilled technical personnel.

Means for Solving the Problem

The inventors have studied hard and consequently found that a series of simple operations without liver biopsy can support detection of NASH by using the amount of LDL-TG contained in a test blood sample isolated from a living body in combination with the amount of at least one component selected from the group consisting of LDL-C, LDL subfraction-C, HDL-C, HDL subfraction-C, ApoB, ApoE, total cholesterol, ALT, and AST contained in the test blood sample, and the inventors completed the invention.

That is, the present invention is as follows.

[1] A method of assisting the detection of nonalcoholic steatohepatitis, the method comprising:

a) measuring the amount of LDL-TG contained in a test blood sample isolated from a living body;

b) measuring the amount of at least one component selected from the group consisting of LDL-C, LDL subfraction-C, HDL-C, HDL subfraction-C, ApoB, ApoE, total cholesterol, ALT, and AST contained in the test blood sample; and c) determining the possibility of developing and/or having nonalcoholic steatohepatitis by using the amount of LDL-TG in combination with the amount of the at least one component.

[2] The method according to [1], wherein the LDL subfraction-C is small dense (sd) LDL-C.

[3] The method according to [1], wherein the HDL subfraction-C is ApoE containing HDL-C and/or HDL2-C and/or HDL3-C.

[4] The method according to any of [1] to [3], further comprising generating a mathematical model with parameters, which are the amount of LDL-TG and the amount of at least one component selected from the group consisting of LDL-C, LDL subfraction-C, HDL-C, HDL subfraction-C, ApoB, ApoE, total cholesterol, ALT, and AST, and substituting the amount of LDL-TG and the amount of the at least one component contained in the test blood sample into the mathematical model to calculate a score, wherein the possibility of having nonalcoholic steatohepatitis is determined to be high when the score is higher than that calculated from the amounts in blood samples from patients with nonalcoholic fatty liver.

[5] A method of generating a mathematical model to determine an index which is for assisting the detection of nonalcoholic steatohepatitis, the method comprising measuring the amount of LDL-TG and the amount of at least one component selected from the group consisting of LDL-C, LDL subfraction-C, HDL-C, HDL subfraction-C, ApoB, ApoE, total cholesterol, ALT, and AST in blood samples from a patient with nonalcoholic steatohepatitis and a patient with nonalcoholic fatty liver, and generating a mathematical model in which the measured amounts are used as parameters.

[6] A measurement kit for use in the method according to any of [1] to [4] for assisting the detection of nonalcoholic steatohepatitis, the measurement kit comprising a reagent for measuring LDL-TG and a reagent for measuring at least one component selected from the group consisting of LDL-C, LDL subfraction-C, HDL-C, HDL subfraction-C, ApoB, ApoE, total cholesterol, ALT, and AST.

[7] The kit according to [6], wherein the LDL subfraction-C is small dense (sd) LDL-C.

[8] The kit according to [6], wherein the HDL subfraction-C is ApoE containing HDL-C and/or HDL2-C and/or HDL3-C.

[9] Use of the kit according to any of [1] to [4] as a kit for assisting the detection of nonalcoholic steatohepatitis.

Effect of the Invention

The invention allows for assistance in detection of NASH through safe and simple operations that do not require skilled technical personnel, while avoiding use of liver biopsy, which causes a significant burden or risk to patients, as much as possible. Consequently, treatment can be started earlier in the course of NASH, which can prevent or delay disease progression to sever stages or death.

DETAIL DESCRIPTION OF THE INVENTION

Figure 1:
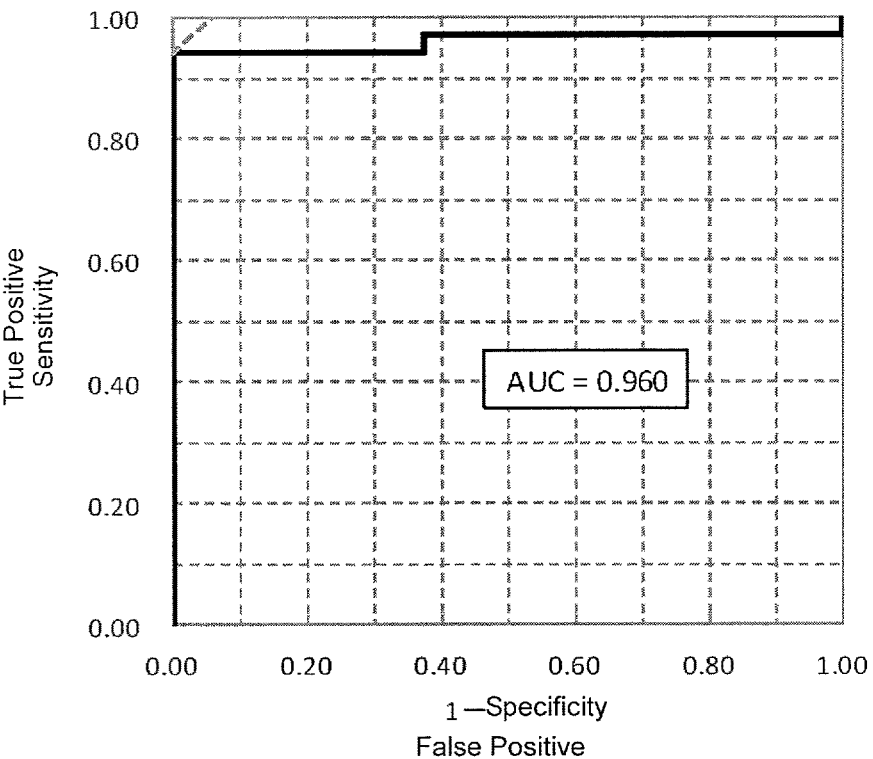
FIG. 1 shows a ROC curve for a mathematical model into which the amounts of LDL-TG, sdLDL-C, HDL2-C, ApoE, and ALT in a blood sample collected from a test subject are substituted for diagnosis of NASH or NAFL in Example 20.

The invention is a method of assisting the detection of NASH, at least based on the amount of LDL-TG contained in a test blood sample isolated from a living body in combination with the amount of at least one component selected from the group consisting of LDL-C, LDL subfraction-C, HDL-C, HDL subfraction-C, ApoB, ApoE, total cholesterol, ALT, and AST contained in the test blood sample. The method of the invention can assist the detection of NASH at higher accuracy levels than a method using only a single conventional liver disease marker such as ALT or LDL-TG.

The at least one component selected from the group consisting of LDL-C, LDL subfraction-C, HDL-C, HDL subfraction-C, ApoB, ApoE, total cholesterol, ALT, and AST contained in the test blood sample may be any one or more components selected from the same group.

In the present invention, LDL-TG indicates triglycerides (TG) in low-density lipoprotein (hereinafter referred to as LDL). LDL-C indicates cholesterol (C) in low-density lipoprotein (LDL). LDL subfractions are fractions of LDL that are subclassified based on particle size, density, or component, including sdLDL, large-buoyant (lb) LDL, and the like. LDL subfraction-C indicates cholesterol (C) in an LDL subfraction. sdLDL-C indicates cholesterol (C) in LDL particles with smaller size and higher density (d=1.044 to 1.063 g/mL). HDL-C indicates cholesterol (C) in high-density lipoprotein (HDL). HDL subfractions are fractions of HDL subclassified based on particle size, density, or component, including HDL2, HDL3, ApoE-containing HDL, and the like. HDL subfraction-C indicates cholesterol (C) in an HDL subfraction. HDL2-C indicates cholesterol (C) in HDL particles with larger size and lower density (d=1.063 to 1.125 g/mL), and HDL3-C indicates cholesterol (C) in HDL with higher density (d=1.125 to 1.210 g/mL). ApoE-containing HDL-C indicates cholesterol (C) in high-density lipoprotein containing a large amount of apolipoprotein E (hereinafter referred to as ApoE-containing HDL). ApoB indicates apolipoprotein B. ApoE indicates apolipoprotein E.

The use of a blood sample as a sample in the present invention is far less invasive than liver biopsy and can provide comprehensive insights into the disease state of the liver as a whole while eliminating dependence on a particular sample removed from the liver. Additionally, collection of a test blood sample is easy, and measurement kits for an automatic analyzer can be used to measure the contents of LDL-TG, LDL-C, sdLDL-C, HDL-C, ApoE-containing HDL-C, HDL2-C, HDL3-C, ApoB, ApoE, total cholesterol, ALT, and AST in the blood sample by a technique as easy as routine medical or physical check-up or other procedures. The blood sample in the present invention includes a whole blood sample, a plasma sample, and a serum sample.

A specific method of assisting the detection of NASH in the present invention will be described below.

In the present invention, the amount of LDL-TG contained in a test blood sample isolated from a living body is measured. In addition, the amount of at least one component selected from the group consisting of LDL-C, LDL subfraction-C, HDL-C, HDL subfraction-C, ApoB, ApoE, total cholesterol, ALT, and AST contained in the test blood sample is measured. Then, the measured amounts of LDL-TG and of the at least one component are combined to determine an index which is for assisting the detection of NASH.

In order to obtain a result that assists the detection of NASH by this invention, a combination of statistical procedures as known to those skilled in the art are applied to the obtained data (the contents of the components in the blood) for analysis, from which a score is calculated. For example, a method of calculating the score comprises selecting a combination of parameters effective for assistance in NASH detection from the many parameters (the contents of the components in the blood), using the selected combination of parameters to generate a mathematical model, and substituting the amount of each component in a test blood sample into the mathematical model.

The amounts of the components in the test blood sample used for the generation of a mathematical model include raw measured values as continuous variables, continuous variables obtained by transforming the measured values, for example, by logarithmic transformation, binary variables created by dichotomizing the measured values at each given value, or nominal or ordered variables created by assigning the measured values to any of three or more classes separated by multiple given values. Any of the variables may be used as the amounts though the amounts are not limited to any of the above variables. Specifically, the measured values of the components should be compared with given values in cases where binary variables are used, and each component whose measured value of amount is smaller or larger than a given value will be provided with an amount of 0 or 1. In this respect, for example, a cutoff value determined by the Youden's index applied to a ROC curve, which is established for the diagnosis of NASH and NAFL based on each single component, can be used as the given value. The Youden's index is a measure to specify a cutoff value by selecting the farthest point on a ROC curve from the diagonal line representing an AUC of 0.500, which is the point giving the maximum value of [sensitivity+(specificity−1)].

Examples of a technique to select a combination of parameters effective for assistance in NASH detection include, but are not limited to, forward and backward stepwise selection, Losso regularization, and elastic net regularization.

After the selection of the combination of effective parameters, an optimal mathematical model for assisting the detection of NASH is generated by an appropriate approach, such as regression analysis. Examples of the approach for generating a mathematical model include, but are not limited to, least squares method, linear discriminant analysis, logistic regression, maximum likelihood method, Lasso regression, Ridge regression, and elastic net regression.

In the present invention, an example of the mathematical model for calculating a score, which is an index for assisting the detection of NASH, is illustrated by the general formula (1) below:

$$\text{Score} = a + b \times [\text{the amount of LDL-TG}] + c \times [\text{the amount of LDL-C}] + d \times [\text{the amount of sdLDL-C}] + e \times [\text{the amount of HDL-C}] + f \times [\text{the amount of ApoE-containing HDL-C}] + g \times [\text{the amount of HDL2-C}] + h \times [\text{the amount of HDL3-C}] + i \times [\text{the amount of ApoB}] + j \times [\text{the amount of ApoE}] + k \times [\text{the amount of total cholesterol}] + l \times [\text{the amount of ALT}] + m \times [\text{the amount of AST}] \quad (1)$$

(in the formula (1), a represents an intercept, and b to m represent coefficients to respective measured values, where a to In may represent products of each number from a to in multiplied by the absolute value of itself).

In cases where raw measured amount values are used as continuous variables for the above general formula (1), the intercept a is preferably a number of −10 to 10, more preferably a number of −5 to 5; the coefficient b is preferably a number of 0.1 to 1.5, more preferably a number of 0.2 to 1.0; the coefficient c is preferably a number of −1.0 to 0, more preferably a number of −0.1 to 0; the coefficient d is preferably a number of −1 to 0, more preferably a number of −0.5 to 0; the coefficient e is preferably a number of −1.0 to 0, more preferably a number of −0.2 to 0, still more preferably a number of −0.1 to 0; the coefficientfis preferably a number of −2 to 0, more preferably a number of −1.5 to 0; the coefficient g is preferably a number of −1.0 to 0, more preferably a number of −0.3 to 0; the coefficient his preferably a number of −1.0 to 0, more preferably a number of −0.2 to 0; the coefficient i is preferably a number of −1.0 to 0, more preferably a number of −0.2 to 0; the coefficient j is preferably a number of 0 to 10, more preferably a number of 0 to 5; the coefficient k is preferably a number of −1.0 to 0, more preferably a number of −0.1 to 0; the coefficient l is preferably a number of −1.0 to 0, more preferably a number of −0.1 to 0; the coefficient m is preferably a number of −1.0 to 0, more preferably a number of −0.2 to 0.

In cases where binary variables created by dichotomization at each given value are used as amounts for the above general formula (1) and the given values are, for example, those used in Comparative Examples 3 and 4, Examples 21 to 36, and Examples 53 to 57, i.e. 17.6 mg/dL for LDL-TG, 116 mg/dL for LDL-C, 34.3 mg/dL for sdLDL-C, 47 mg/dL for HDL-C, 43.8 mg/dL for HDL2-C, 22.7 mg/dL for HDL3-C, 4.2 mg/dL for ApoE-containing HDL-C (AE-HDL), 88.9 mg/dL for ApoB, 3.4 mg/dL for ApoE, 178 mg/dL for total cholesterol (TC), 32 units for ALT, and 20 units for AST, the intercept a is preferably a number of −100 to 100, more preferably a number of 0 to 40; the coefficient b is preferably a number of 1 to 10, more preferably a number of 2 to 5; the coefficient c is preferably a number of −5.0 to 0, more preferably a number of −3 to 0; the coefficient d is preferably a number of −5 to 0, more preferably a number of −4 to 0, still more preferably a number of −3 to 0; the coefficient e is preferably a number of −30 to 0, more preferably a number of −20 to 0; the coefficient f is preferably a number of −30 to 0, more preferably a number of −20 to 0; the coefficient g is preferably a number of −5 to 0, more preferably a number of −3 to 0; the coefficient h is preferably a number of −30 to 0, more preferably a number of −20 to 0; the coefficient i is preferably a number of −5 to 0, more preferably a number of −3 to 0; the coefficient j is preferably a number of 0 to 10, more preferably a number of 0 to 3; the coefficient k is preferably a number of −30 to 0, more preferably a number of −20 to 0; the coefficient l is preferably a number of −5 to 0, more preferably a number of −2 to 0; the coefficient m is preferably a number of −5 to 0, more preferably a number of −2 to 0.

The above general formula (1) is an example mathematical model in this invention, and a mathematical model generated by modifying the above general formula (1) may be used, wherein each value of the intercept a and the coefficients b to m is multiplied by the absolute value of itself, or wherein an arbitrary number is added to or subtracted from the value of the intercept a. Moreover, any value can be selected as the threshold for transformation into binary variables. Thus, the intercept and coefficients of the mathematical model used in the present invention will not be limited to the above-described ranges.

A score can be calculated by substituting the amount of each component into a generated mathematical model, as described for the above general formula (1). The obtained score can be compared with a reference value to indicate a high possibility of having NASH when the score is larger than the reference value or to indicate a low possibility of having NASH when the score is smaller than the reference value. The reference value can be arbitrarily set considering the sensitivity, the specificity, the positive predictive value (PPV), and the negative predictive value (NPV) for different purposes. For example, the reference value can be set to a lower value for reducing the frequency of false negative results and to a higher value for reducing the frequency of false positive results. In the present invention, Youden's index, which is considered as a measure of providing a good balance between those properties, is used for setting a reference value. However, the reference value described in the present invention is merely an example, and other values can be used as the reference value for different purposes, as described above. Moreover, the optimal reference value varies among different populations of patients from whom data are collected. Furthermore, the optimal reference value varies according as each of the coefficients and intercept in the mathematical model is multiplied by the absolute value of itself or according as an arbitrary number is added to or subtracted from the intercept in the mathematical model, as described above.

In the present invention, area under ROC curve (AUC: area under curve) and accuracy (the proportion of correctly predicted NASH or NAFL in test patients) are used as indicators which represent the accuracy of NASH detection. In respect of AUC, an AUC of not less than 0.80 means high accuracy, and an AUC of not less than 0.85 means very high accuracy, and an AUC of not less than 0.90 means quite high accuracy. Thus, a mathematical model in the present invention also preferably has an AUC of not less than 0.80, more preferably not less than 0.85, much more preferably not less than 0.90. In respect of accuracy, an accuracy of not less than 75% means high accuracy, and an accuracy of not less than 85% means very high accuracy, and an accuracy of not less than 95% means quite high accuracy. Thus, a mathematical model in the present invention also preferably has an accuracy of not less than 75%, more preferably an accuracy of not less than 85%, much more preferably an accuracy of not less than 95%.

Among the components in a test blood sample, a combination of LDL-TG, sdLDL-C, HDL2-C, ApoE, and ALT (Example 20 below) and a combination of LDL-TG, HDL2-C, ApoE, and total cholesterol (Example 36 below) can be used for cases that involve using the measured amount values directly and for cases that involve dichotomizing the measured amount values to use the resulting binary variables, respectively, to achieve an AUC of not less than 0.90 and an accuracy of 95%, so that NASH can be detected with quite high accuracy.

In the present invention, the possibility of developing NASH can be determined without using a mathematical model as described above, by using the amount of LDL-TG contained in a test blood sample in combination with the amount of at least one component selected from the group consisting of LDL-C, LDL subfraction-C, HDL-C, HDL subfraction-C, ApoB, ApoE, total cholesterol, ALT, and AST contained in the test blood sample and analyzing whether the amount of each component in the combination is equal to or above the cutoff value of the component or is equal to or below the cutoff value of the component. The cutoff values can be determined, for example, using the Youden's index applied to the ROC curves for diagnosis of NASH and NAFL based on each of the single components.

Specifically, the possibility of developing NASH can be determined to be high when the amount of LDL-TG is equal to or above the cutoff value of the test item and the amount of any test item selected from LDL-C, LDL subfraction-C, HDL-C, HDL subfraction-C, ApoB, total cholesterol, ALT, and AST is equal to or below the cutoff value of the test item, or when the amount of LDL-TG contained in a test blood sample is equal to or above the cutoff value of the test item and the amount of ApoE is equal to or above the cutoff value of the test item, where the cutoff values are those used in Examples 37 to 47, i.e. 17.6 mg/dL for LDL-TG, 116 mg/dL for LDL-C, 34.3 mg/dL for sdLDL-C, 47 mg/dL for HDL-C, 43.8 mg/dL for HDL2-C, 22.7 mg/dL for HDL3-C, 4.2 mg/dL for ApoE-containing HDL-C (AE-HDL), 88.9 mg/dL for ApoB, 3.4 mg/dL for ApoE, 178 mg/dL for total cholesterol (TC), 32 units for ALT, and 20 units for AST. However, the cutoff value can be arbitrarily set for different purposes, such as taking priority on sensitivity or specificity. The combination of test items is not limited to that described above, though the cutoff values are usually set to values in the range of ±50%, more preferably ±30%, of the above-described values used in Examples 37 to 47 (the values described in Table 5).

The combinational use as described above, in which the amount of LDL-TG contained in a test blood sample is combined with the amount of at least one component selected from the group consisting of LDL-C, LDL subfraction-C, HDL-C, HDL subfraction-C, ApoB, ApoE, total cholesterol, ALT, and AST contained in the test blood sample, allows for easy and highly accurate detection of NASH and NAFL through simple operations, for which liver biopsy is conventionally required.

The present invention also provides a method of detecting LDL-TG and at least one component selected from the group consisting of LDL-C, LDL subfraction-C, HDL-C, HDL subfraction-C, ApoB, ApoE, total cholesterol, ALT, and AST in a test blood sample from a human subject who is suspected of having nonalcoholic steatohepatitis or has a risk of nonalcoholic steatohepatitis.

That is, the present invention also provides a method of detecting LDL-TG and at least one component selected from the group consisting of LDL-C, LDL subfraction-C, HDL-C, HDL subfraction-C, ApoB, ApoE, total cholesterol, ALT, and AST in a test blood sample from a human subject who is suspected of having nonalcoholic steatohepatitis or has a risk of nonalcoholic steatohepatitis, wherein the method comprises the steps of:

collecting a blood sample from the human subject; and measuring the amount of LDL-TG and the amount of at least one component selected from the group consisting of LDL-C, LDL subfraction-C, HDL-C, HDL subfraction-C, ApoB, ApoE, total cholesterol, ALT, and AST in the blood sample, wherein a score is calculated by substituting the amount of LDL-TG and the amount of the at least one component contained in the blood sample into a mathematical model, which is generated with parameters that represent the amount of LDL-TG and the amount of the at least one component, and the score is higher than that calculated from the amounts in blood samples from patients with nonalcoholic fatty liver.

Once nonalcoholic steatohepatitis is detected with the help of the method of the invention as described above, an effective amount of a therapeutic agent for nonalcoholic steatohepatitis can be administered to a patient detected with nonalcoholic steatohepatitis to treat the patient's nonalcoholic steatohepatitis. The therapeutic agent can be pioglitazone for cases with diabetes, vitamin E for cases without diabetes, or the like.

In the present invention, a conventionally known technique can be used for the procedure of measuring the contents of LDL-C, sdLDL-C, HDL2-C, HDL3-C, HDL-C, ApoE-containing HDL-C, ApoB, ApoE, total cholesterol, ALT, and AST in a blood sample. For example, the procedure of measuring various lipid components includes a method comprising separating a target lipoprotein by a fractionation procedure, such as ultracentrifugation, electrophoresis, or high-performance liquid chromatography, and subsequently quantifying triglycerides and/or cholesterol by a quantitative technique, and a method comprising not conducting the fractionation procedure but removing triglycerides and cholesterol in lipoproteins other than those in a target lipoprotein during the first step and subsequently quantifying triglycerides and/or cholesterol in the target lipoprotein during the second step, and other methods. The procedure of measuring ApoB or ApoE includes ELISA or immunoturbidimetry using an antibody against either of them. The procedure of measuring ALT includes the LDH-UV test (a JSCC standard operating procedure), and the procedure of measuring AST includes the MDH-UV test (a JSCC standard operating procedure).

Specifically, the procedure described in WO2013/157642 can be used as a method of measuring the LDL-TG content, and the procedure described in WO98/47005 can be used as a method of measuring the LDL-C content, and the procedure described in WO08/105486 can be used as a method of measuring the sdLDL-C content, and the procedure described in WO98/26090 can be used as a method of measuring the HDL-C content, and the procedure described in Ito Y. et al. (2014) "Development of a homogeneous assay for measurement of high-density lipoprotein-subclass cholesterol," Clinica Chimica Acta, 427: 86-93 can be used as a method of measuring the HDL2-C content and the HDL3-C content, and the procedure described in JP 2014-030393 A can be used as a method of measuring the ApoE-containing HDL-C content. However, those methods are not limited to the procedures described above, provided that those test items are measured by those methods.

The invention is specifically described below by way of example, but the invention will not be limited to the examples below.

EXAMPLES

The contents of LDL-TG, LDL-C, sdLDL-C, HDL-C, HDL2-C, HDL3-C, ApoE-containing HDL-C, ApoB, ApoE, total cholesterol, ALT, and AST were measured in blood samples collected from a population of 8 patients with NAFL and 34 patients with NASA, 42 subjects in total, by using an automatic analyzer. Different assay reagents for automatic analyzers commonly used in clinical laboratory settings were used for the measurement of LDL-C, HDL-C, ApoB, ApoE, total cholesterol, ALT, and AST contents. LDLTG-EX "SEIKEN" (manufactured by Denka Seiken Co., Ltd.), sdLDL-EX "SEIKEN" (manufactured by Denka Seiken Co., Ltd.), the procedure described in Ito Y, et al. (2014) "Development of a homogeneous assay for measurement of high-density lipoprotein-subclass cholesterol," Clinica Chimica Acta, 427: 86-93, and the procedure described in JP 2014-030393 A were used for the measurement of LDL-TG content, sdLDL-C content, HDL2-C and HDL3-C contents, and ApoE-containing HDL-C content, respectively.

Comparative Examples 1 and 2, Examples 1 to 20

In Comparative Examples 1 and 2 and Examples 1 to 20, the items shown in Table 1 were used, and the raw measured values of the respective items as continuous variables were used as the amounts of the items.

TABLE 1

| No. | Item |
|---|---|
| Comparative Example 1 | ALT |
| Comparative Example 2 | LDL-TG |
| Example 1 | LDL-TG, LDL-C |
| Example 2 | LDL-TG, ApoB |
| Example 3 | LDL-TG, sdLDL-C, ALT |
| Example 4 | LDL-TG, TC, ALT |
| Example 5 | LDL-TG, AE-HDL, ApoB |
| Example 6 | LDL-TG, sdLDL-C, HDL-C |
| Example 7 | LDL-TG, LDL-C, HDL-C |
| Example 8 | LDL-TG, HDL-C, ApoB |
| Example 9 | LDL-TG, HDL3-C, ApoB, AST |
| Example 10 | LDL-TG, ApoE, TC, ALT |
| Example 11 | LDL-TG, sdLDL-C, ApoE, ALT |
| Example 12 | LDL-TG, sdLDL-C, HDL2-C, AST |
| Example 13 | LDL-TG, sdLDL-C, AE-HDL, ALT |
| Example 14 | LDL-TG, sdLDL-C, HDL-C, ALT |
| Example 15 | LDL-TG, HDL3-C, ApoB, ALT |
| Example 16 | LDL-TG, sdLDL-C, HDL2-C, ALT |
| Example 17 | LDL-TG, HDL2-C, ApoB, ALT |
| Example 18 | LDL-TG, sdLDL-C, AE-HDL, ApoE, ALT |
| Example 19 | LDL-TG, sdLDL-C, HDL2-C, ApoE, AST |
| Example 20 | LDL-TG, sdLDL-C, HDL2-C, ApoE, ALT |

AE-HDL: ApoE-containing HDL-C,

TC: total cholesterol

Mathematical models established by logistic regression analysis in the respective combinations are shown in Table 2. A score is calculated by substituting the measured value of each item for the variable represented by the name of the item in each mathematical model.

TABLE 2

| No. | Mathematical model |
|---|---|
| Comparative Example 1 | $+1.861 - 0.009\text{ALT}$ |
| Comparative Example 2 | $-2.374 + 0.228\text{LDL-TG}$ |
| Example 1 | $-0.119 + 0.381\text{LDL-TG} - 0.042\text{LDL-C}$ |
| Example 2 | $+0.568 + 0.418\text{LDL-TG} - 0.067\text{ApoB}$ |
| Example 3 | $-2.064 + 0.454\text{LDL-TG} - 0.090\text{sdLDL-C} - 0.018\text{ALT}$ |
| Example 4 | $+3.258 + 0.560\text{LDL-TG} - 0.05\text{ ITC} - 0.020\text{ALT}$ |
| Example 5 | $+3.375 + 0.473\text{LDL-TG} - 0.483\text{AE-HDL} - 0.077\text{ApoB}$ |
| Example 6 | $+2.215 + 0.392\text{LDL-TG} - 0.109\text{sdLDL-C} - 0.055\text{HDL-C}$ |
| Example 7 | $+2.559 + 0.410\text{LDL-TG} - 0.047\text{LDL-C} - 0.040\text{HDL-C}$ |
| Example 8 | $+4.375 + 0.485\text{LDL-TG} - 0.054\text{HDL-C} - 0.084\text{ApoB}$ |
| Example 9 | $+3.941 + 0.582\text{LDL-TG} - 0.131\text{HDL3-C} - 0.082\text{ApoB} - 0.038\text{AST}$ |
| Example 10 | $+0.673 + 0.537\text{LDL-TG} + 1.028\text{ApoE} - 0.056\text{TC} - 0.022\text{ALT}$ |
| Example 11 | $-4.591 + 0.426\text{LDL-TG} - 0.097\text{sdLDL-C} + 0.873\text{ApoE} - 0.020\text{ALT}$ |
| Example 12 | $+3.155 + 0.668\text{LDL-TG} - 0.181\text{sdLDL-C} - 0.114\text{HDL2-C} - 0.056\text{AST}$ |
| Example 13 | $+1.513 + 0.569\text{LDL-TG} - 0.125\text{sdLDL-C} - 0.685\text{AE-HDL} - 0.022\text{ALT}$ |
| Example 14 | $+3.140 + 0.592\text{LDL-TG} - 0.145\text{sdLDL-C} - 0.082\text{HDL-C} - 0.023\text{ALT}$ |
| Example 15 | $+2.843 + 0.536\text{LDL-TG} - 0.120\text{HDL3-C} - 0.071\text{ApoB} - 0.016\text{ALT}$ |
| Example 16 | $+2.272 + 0.627\text{LDL-TG} - 0.159\text{sdLDL-C} - 0.115\text{HDL2-C} - 0.024\text{ALT}$ |
| Example 17 | $+3.727 + 0.716\text{LDL-TG} - 0.097\text{HDL2-C} - 0.102\text{ApoB} - 0.021\text{ALT}$ |
| Example 18 | $-1.302 + 0.682\text{LDL-TG} - 0.205\text{sdLDL-C} - 1.299\text{AE-HDL} + 2.205\text{ApoE} - 0.034\text{ALT}$ |
| Example 19 | $-0.058 + 0.941\text{LDL-TG} - 0.356\text{sdLDL-C} - 0.244\text{HDL2-C} + 3.273\text{ApoE} - 0.113\text{AST}$ |
| Example 20 | $-1.512 + 0.819\text{LDL-TG} - 0.279\text{sdLDL-C} - 0.216\text{HDL2-C} + 2.652\text{ApoE} - 0.041 \text{ ALT}$ |

AE-HDL: ApoE-containing HDL-C,

TC: total cholesterol

The areas under ROC curves (AUC) for prediction of subjects positive for NASH, reference values determined by the Youden's index for each ROC curve, and the values of sensitivity, specificity, PPV (positive predictive value), NPV (negative predictive value), and accuracy determined by comparison between each reference value and each score are shown in Tables 3-1 and 3-2. Additionally, the ROC curve of Example 20 is shown in FIG. 1 as a representative example.

TABLE 3-1

| No. | Item | AUC | Reference value | Sensitivity | Specificity | PPV | NPV | Accuracy |
|---|---|---|---|---|---|---|---|---|
| Comparative Example 1 | ALT | 0.500 | 1.565 | 64.7% | 50.0% | 84.6% | 25.0% | 61.9% |
| Comparative Example 2 | LDL-TG | 0.787 | 1.638 | 64.7% | 87.5% | 95.7% | 36.8% | 69.0% |
| Example 1 | LDL-TG LDL-C | 0.838 | 0.950 | 94.1% | 62.5% | 91.4% | 71.4% | 88.1% |
| Example 2 | LDL-TG ApoB | 0.849 | −0.323 | 100.0% | 62.5% | 91.9% | 100.0% | 92.9% |
| Example 3 | LDL-TG sdLDL-C ALT | 0.886 | 1.851 | 79.4% | 87.5% | 96.4% | 50.0% | 81.0% |
| Example 4 | LDL-TG TC ALT | 0.912 | 1.140 | 88.2% | 87.5% | 96.8% | 63.6% | 88.1% |
| Example 5 | LDL-TG AE-HDL ApoB | 0.871 | 0.671 | 94.1% | 75.0% | 94.1% | 75.0% | 90.5% |
| Example 6 | LDL-TG sdLDL-C HDL-C | 0.875 | 0.524 | 94.1% | 75.0% | 94.1% | 75.0% | 90.5% |
| Example 7 | LDL-TG LDL-C HDL-C | 0.875 | 0.726 | 94.1% | 75.0% | 94.1% | 75.0% | 90.5% |
| Example 8 | LDL-TG HDL-C ApoB | 0.879 | 0.792 | 94.1% | 75.0% | 94.1% | 75.0% | 90.5% |
| Example 9 | LDL-TG HDL3-C ApoB AST | 0.915 | 1.492 | 85.3% | 87.5% | 96.7% | 58.3% | 85.7% |
| Example 10 | LDL-TG ApoE TC ALT | 0.945 | 2.099 | 85.3% | 100.0% | 100.0% | 61.5% | 88.1% |
| Example 11 | LDL-TG sdLDL-C ApoE ALT | 0.908 | −0.102 | 94.1% | 75.0% | 94.1% | 75.0% | 90.5% |
| Example 12 | LDL-TG sdLDL-C HDL2-C AST | 0.912 | 0.941 | 91.2% | 87.5% | 96.9% | 70.0% | 90.5% |

TABLE 3-2

| No. | Item | AUC | Reference value | Sensitivity | Specificity | PPV | NPV | Accuracy |
|---|---|---|---|---|---|---|---|---|
| Example 13 | LDL-TG sdLDL-C AE-HDL ALT | 0.919 | 1.255 | 91.2% | 87.5% | 96.9% | 70.0% | 90.5% |
| Example 14 | LDL-TG sdLDL-C HDL-C ALT | 0.919 | 1.375 | 91.2% | 87.5% | 96.9% | 70.0% | 90.5% |
| Example 15 | LDL-TG HDL3-C ApoB ALT | 0.912 | −0.274 | 97.1% | 75.0% | 94.3% | 85.7% | 92.9% |
| Example 16 | LDL-TG sdLDL-C HDL2-C ALT | 0.923 | 0.626 | 94.1% | 87.5% | 97.0% | 77.8% | 92.9% |
| Example 17 | LDL-TG HDL2-C ApoB ALT | 0.934 | 1.182 | 94.1% | 87.5% | 97.0% | 77.8% | 92.9% |
| Example 18 | LDL-TG sdLDL-C AE-HDL ApoE ALT | 0.952 | 1.435 | 91.2% | 100.0% | 100.0% | 72.7% | 92.9% |

TABLE 3-2-continued

| No. | Item | AUC | Reference value | Sensitivity | Specificity | PPV | NPV | Accuracy |
|-----|------|-----|-----------------|-------------|-------------|-----|-----|----------|
| Example 19 | LDL-TG sdLDL-C HDL2-C ApoE AST | 0.971 | 0.853 | 91.2% | 100.0% | 100.0% | 72.7% | 92.9% |
| Example 20 | LDL-TG sdLDL-C HDL2-C ApoE ALT | 0.960 | 0.797 | 94.1% | 100.0% | 100.0% | 80.0% | 95.2% |

AE-HDL: ApoE-containing HDL-C, TC: total cholesterol

As shown in Tables 3-1 and 3-2, Examples 1 to 20 provided higher values of AUC and accuracy than those in Comparative Example 1 where only ALT, a conventional liver disease marker, was utilized, and those in Comparative Example 2 where only LDL-TG, another conventional liver disease marker, was utilized, indicating that the development of NASH or NAFL could be predicted with a higher probability.

Comparative Examples 3 and 4, Examples 21 to 36

In Comparative Examples 3 and 4 and Examples 21 to 36, the items shown in Table 4 were used, and binary variables created by dichotomizing each measured value at a cutoff value determined by the Youden's index for an ROC curve based on each single item were used as the amounts of the items.

TABLE 4

| No. | Item |
|-----|------|
| Comparative Example 3 | ALT |
| Comparative Example 4 | LDL-TG |
| Example 21 | LDL-TG, TC |
| Example 22 | LDL-TG, LDL-C |
| Example 23 | LDL-TG, sdLDL-C, AE-HDL |
| Example 24 | LDL-TG, ApoE, TC |
| Example 25 | LDL-TG, ApoB, ALT |
| Example 26 | LDL-TG, sdLDL-C, ALT |
| Example 27 | LDL-TG, LDL-C, ApoE |
| Example 28 | LDL-TG, LDL-C, ALT |
| Example 29 | LDL-TG, HDL-C, TC |
| Example 30 | LDL-TG, AE-HDL, TC |
| Example 31 | LDL-TG, ApoB, ApoE, AST |
| Example 32 | LDL-TG, ApoE, TC, AST |
| Example 33 | LDL-TG, sdLDL-C, HDL-C, ApoE |
| Example 34 | LDL-TG, sdLDL-C, HDL3-C, ALT |
| Example 35 | LDL-TG, sdLDL-C, HDL2-C, HDL3-C |
| Example 36 | LDL-TG, HDL2-C, ApoE, TC |

AE-HDL: ApoE-containing HDL-C,
TC: total cholesterol

The cutoff values for the respective items used in Comparative Examples 3 and 4 and Examples 21 to 36 are shown in Table 5.

TABLE 5

| Item | Cutoff value |
|------|--------------|
| LDL-TG | 17.6 mg/dL |
| LDL-C | 116 mg/dL |
| sdLDL-C | 34.3 mg/dL |
| HDL-C | 47 mg/dL |
| HDL2-C | 43.8 mg/dL |

TABLE 5-continued

| Item | Cutoff value |
|------|--------------|
| HDL3-C | 22.7 mg/dL |
| AE-HDL | 4.2 mg/dL |
| ApoB | 88.9 mg/dL |
| ApoE | 3.4 mg/dL |
| TC | 178 mg/dL |
| ALT | 32 units |
| AST | 20 units |

AE-HDL: ApoE-containing HDL-C,
TC: total cholesterol

Mathematical models established by logistic regression analysis in the respective combinations are shown in Table 6. A score is calculated by substituting the value of each item for the variable represented by the name of the item in each mathematical model, where a value of 1 or 0 is substituted depending on whether the measured value of the item is larger or smaller than the cutoff value of the item.

TABLE 6

| No. | Mathematical model |
|-----|--------------------|
| Comparative Example 3 | $1.705 - 0.606ALT$ |
| Comparative Example 4 | $0.539 + 2.552LDL\text{-}TG$ |
| Example 21 | $16.200 + 2.719LDL\text{-}TG - 16.354TC$ |
| Example 22 | $1.579 + 3.017LDL\text{-}TG - 2.154LDL\text{-}C$ |
| Example 23 | $18.522 + 2.755LDL\text{-}TG - 2.328sdLDL\text{-}C - 17.194AE\text{-}HDL$ |
| Example 24 | $15.865 + 2.983LDL\text{-}TG + 2.057ApoE - 17.533TC$ |
| Example 25 | $1.625 + 3.197LDL\text{-}TG - 1.443ApoB - 1.115\ ALT$ |
| Example 26 | $1.711 + 2.980LDL\text{-}TG - 1.563sdLDL\text{-}C - 1.167ALT$ |
| Example 27 | $0.306 + 3.132LDL\text{-}TG - 2.157LDL\text{-}C + 1.791ApoE$ |
| Example 28 | $1.924 + 3.507LDL\text{-}TG - 2.051LDL\text{-}C - 1.386ALT$ |
| Example 29 | $33.270 + 2.416LDL\text{-}TG - 16.307HDL\text{-}C - 17.299TC$ |
| Example 30 | $32.653 + 2.416LDL\text{-}TG - 16.001AE\text{-}HDL - 16.989TC$ |
| Example 31 | $0.754 + 3.114LDL\text{-}TG - 2.093ApoB + 2.205ApoE - 0.826AST$ |
| Example 32 | $16.862 + 3.321LDL\text{-}TG + 2.518ApoE - 17.977TC - 1.27AST$ |
| Example 33 | $17.162 + 2.604LDL\text{-}TG - 2.789sdLDL\text{-}C - 16.987HDL\text{-}C + 2.073ApoE$ |
| Example 34 | $18.786 + 3.016LDL\text{-}TG - 1.864sdLDL\text{-}C - 17.446HDL3\text{-}C - 1.595ALT$ |
| Example 35 | $19.209 + 3.238LDL\text{-}TG - 2.869sdLDL\text{-}C - 2.833HDL2\text{-}C - 17.123HDL3\text{-}C$ |
| Example 36 | $16.382 + 3.207LDL\text{-}TG - 1.803HDL2\text{-}C + 2.013ApoE - 17.636TC$ |

AE-HDL: ApoE-containing HDL-C,
TC: total cholesterol

Figure 2:
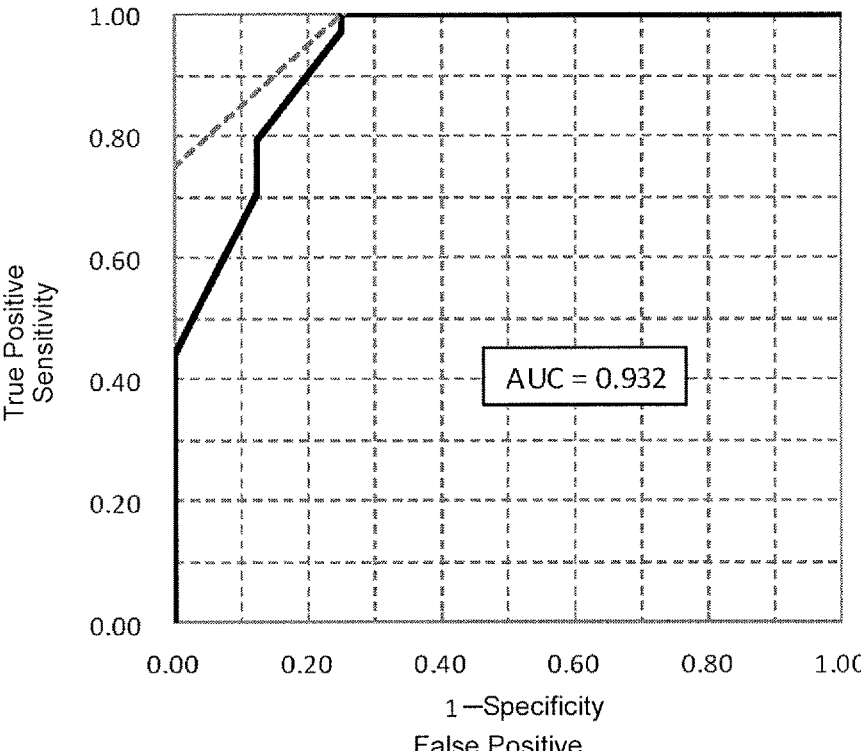
FIG. 2 shows a ROC curve for a mathematical model into which binary variables obtained by dichotomizing the amounts of LDL-TG, HDL2-C, ApoE, and total cholesterol in a blood sample collected from a test subject at the cutoff value of each item are substituted for diagnosis of NASH or NAFL in Example 36.

The areas under ROC curves (AUC) for prediction of subjects positive for NASH, reference values determined by the Youden's index for each ROC curve, and the values of sensitivity, specificity, PPV (positive predictive value), NPV (negative predictive value), and accuracy determined by comparison between each reference value and each score are shown in Tables 7-1 and 7-2. Additionally, the ROC curve of Example 36 is shown in FIG. 2 as a representative example.

TABLE 7-1

| No. | Item | AUC | Reference value | Sensitivity | Specificity | PPV | NPV | Accuracy |
|---|---|---|---|---|---|---|---|---|
| Comparative Example 3 | ALT | 0.574 | 1.705 | 64.7% | 50.0% | 84.6% | 25.0% | 61.9% |
| Comparative Example 4 | LDL-TG | 0.761 | 3.091 | 64.7% | 87.5% | 95.7% | 36.8% | 69.0% |
| Example 21 | LDL-TG TC | 0.877 | 2.565 | 82.4% | 87.5% | 96.6% | 53.8% | 83.3% |
| Example 22 | LDL-TG LDL-C | 0.855 | 1.579 | 91.2% | 62.5% | 91.2% | 62.5% | 85.7% |
| Example 23 | LDL-TG sdLDL-C AE-HDL | 0.899 | 1.756 | 73.5% | 87.5% | 96.2% | 43.8% | 76.2% |
| Example 24 | LDL-TG ApoE TC | 0.915 | 1.315 | 82.4% | 87.5% | 96.6% | 53.8% | 83.3% |
| Example 25 | LDL-TG ApoB ALT | 0.860 | 1.625 | 88.2% | 75.0% | 93.8% | 60.0% | 85.7% |

TABLE 7-2

| No. | Item | AUC | Reference value | Sensitivity | Specificity | PPV | NPV | Accuracy |
|---|---|---|---|---|---|---|---|---|
| Example 26 | LDL-TG sdLDL-C ALT | 0.866 | 1.711 | 88.2% | 75.0% | 93.8% | 60.0% | 85.7% |
| Example 27 | LDL-TG LDL-C ApoE | 0.873 | 1.282 | 88.2% | 75.0% | 93.8% | 60.0% | 85.7% |
| Example 28 | LDL-TG LDL-C ALT | 0.879 | 1.924 | 88.2% | 75.0% | 93.8% | 60.0% | 85.7% |
| Example 29 | LDL-TG HDL-C TC | 0.903 | 2.079 | 85.3% | 87.5% | 96.7% | 58.3% | 85.7% |
| Example 30 | LDL-TG AE-HDL TC | 0.903 | 2.079 | 85.3% | 87.5% | 96.7% | 58.3% | 85.7% |
| Example 31 | LDL-TG ApoB ApoE AST | 0.866 | 0.866 | 88.2% | 75.0% | 93.8% | 60.0% | 85.7% |
| Example 32 | LDL-TG ApoE TC AST | 0.926 | 0.936 | 88.2% | 87.5% | 96.8% | 63.6% | 88.1% |
| Example 33 | LDL-TG sdLDL-C HDL-C ApoE | 0.921 | 2.063 | 91.2% | 75.0% | 93.9% | 66.7% | 88.1% |
| Example 34 | LDL-TG sdLDL-C HDL3-C ALT | 0.943 | 1.340 | 91.2% | 87.5% | 96.9% | 70.0% | 90.5% |
| Example 35 | LDL-TG sdLDL-C HDL2-C HDL3-C | 0.936 | −0.377 | 94.1% | 87.5% | 97.0% | 77.8% | 92.9% |
| Example 36 | LDL-TG HDL2-C ApoE TC | 0.932 | 0.150 | 100.0% | 75.0% | 94.4% | 100.0% | 95.2% |

AE-HDL: ApoE-containing HDL-C, TC: total cholesterol

As shown in Tables 7-1 and 7-2, Examples 21 to 36 provided higher values of AUC and accuracy than those in Comparative Example 3 where only ALT, a conventional liver disease marker, was utilized, and those in Comparative Example 4 where only LDL-TG, another conventional liver disease marker, was utilized, indicating that the development of NASH or NAFL could be predicted with a higher probability.

Examples 37 to 47

In Examples 37 to 47, the items shown in Table 8 were used, and the assessment was performed not using any mathematical model but using combinations of results from studies evaluating whether the amount of each component contained in a test blood sample was equal to or above the cut-off value of the component or was equal to or below the cut-off value of the component. The values shown in Table 5 were used as the cutoff values of the respective items.

TABLE 8

| No. | Item |
| --- | --- |
| Example 37 | LDL-TG, LDL-C |
| Example 38 | LDL-TG, sdLDL-C |
| Example 39 | LDL-TG, HDL-C |
| Example 40 | LDL-TG, HDL2-C |
| Example 41 | LDL-TG, HDL3-C |
| Example 42 | LDL-TG, AE-HDL |
| Example 43 | LDL-TG, ApoB |
| Example 44 | LDL-TG, ApoE |
| Example 45 | LDL-TG, TC |
| Example 46 | LDL-TG, ALT |
| Example 47 | LDL-TG, AST |

AE-HDL: ApoE-containing HDL-C,
TC: total cholesterol

The combinations of measurements of the respective items, the number of subjects, and the percentage of NASH patients in the subjects assessed in Examples 37 to 47 are shown in Table 9.

TABLE 9

| No. | Combination of measurements of the respective items | Number of subjects | Percentage of NASH patients |
| --- | --- | --- | --- |
| Example 37 | LDL-TG content equal to or above its cutoff value and LDL-C content equal to or below its cutoff value | 12 | 100% |
| Example 38 | LDL-TG content equal to or above its cutoff value and sdLDL-C content equal to or below its cutoff value | 13 | 100% |
| Example 39 | LDL-TG content equal to or above its cutoff value and HDL-C content equal to or below its cutoff value | 8 | 100% |
| Example 40 | LDL-TG content equal to or above its cutoff value and HDL2-C content equal to or below its cutoff value | 20 | 95% |
| Example 41 | LDL-TG content equal to or above its cutoff value and HDL3-C content equal to or below its cutoff value | 14 | 100% |
| Example 42 | LDL-TG content equal to or above its cutoff value and AE-HDL content equal to or below its cutoff value | 10 | 100% |

TABLE 9-continued

| No. | Combination of measurements of the respective items | Number of subjects | Percentage of NASH patients |
| --- | --- | --- | --- |
| Example 43 | LDL-TG content equal to or above its cutoff value and ApoB content equal to or below its cutoff value | 10 | 100% |
| Example 44 | LDL-TG content equal to or above its cutoff value and ApoE content equal to or above its cutoff value | 17 | 94% |
| Example 45 | LDL-TG content equal to or above its cutoff value and TC content equal to or below its cutoff value | 9 | 100% |
| Example 46 | LDL-TG content equal to or above its cutoff value and ALT content equal to or below its cutoff value | 12 | 100% |
| Example 47 | LDL-TG content equal to or above its cutoff value and AST content equal to or below its cutoff value | 1 | 100% |

AE-HDL: ApoE-containing HDL-C,
TC: total cholesterol

As shown in Table 9, a high proportion of the subjects who participated in the combinations of measurements in Examples 37 to 47 were found to be NASH patients, indicating that the possibility of developing NASH could be determined by the combinations of measurements of those items.

Examples 48 to 52

In Examples 48 to 52, the items shown in Table 10 were used, and the raw measured values of the respective items as continuous variables were used as the amounts of the items.

TABLE 10

| No. | Item |
| --- | --- |
| Example 48 | LDL-TG, HDL2-C, ApoE, TC |
| Example 49 | LDL-TG, HDL-C, ApoE, TC |
| Example 50 | LDL-TG, sdLDL-C, HDL-C, ApoE, ALT |
| Example 51 | LDL-TG, HDL-C, ApoB, ApoE, ALT |
| Example 52 | LDL-TG, LDL-C, HDL-C, ApoE, ALT |

TC: total cholesterol

Mathematical models established by logistic regression analysis in the respective combinations are shown in Table 11. A score is calculated by substituting the measured value of each item for the variable represented by the name of the item in each mathematical model.

TABLE 11

| No. | Mathematical model |
| --- | --- |
| Example 48 | $+1.850 + 0.388LDL\text{-}TG - 0.017HDL2\text{-}C + 0.745ApoE - 0.047TC$ |
| Example 49 | $+1.906 + 0.384LDL\text{-}TG - 0.011HDL\text{-}C + 0.721 ApoE - 0.046TC$ |
| Example 50 | $+1.501 + 0.719LDL\text{-}TG - 0.244sdLDL\text{-}C - 0.152HDL\text{-}C + 2.248ApoE - 0.036ALT$ |
| Example 51 | $+2.691 + 0.654LDL\text{-}TG - 0.097HDL\text{-}C - 0.105ApoB + 1.181ApoE - 0.023ALT$ |
| Example 52 | $+1.025 + 0.508LDL\text{-}TG - 0.052LDL\text{-}C - 0.072HDL\text{-}C + 0.917ApoE - 0.020ALT$ |

TC: total cholesterol

The areas under ROC curves (AUC) for prediction of subjects positive for NASH, a determined reference value, and the values of sensitivity, specificity, PPV (positive predictive value), NPV (negative predictive value), and accuracy determined by comparison between each reference value and each score are shown in Table 12.

TABLE 12

| No. | Item | AUC | Reference value | Sensitivity | Specificity | PPV | NPV | Accuracy |
|---|---|---|---|---|---|---|---|---|
| Example 48 | LDL-TG HDL2-C ApoE TC | 0.868 | 1.224 | 88.2% | 87.5% | 96.8% | 63.6% | 88.1% |
| Example 49 | LDL-TG HDL-C ApoE TC | 0.871 | 1.129 | 88.2% | 87.5% | 96.8% | 63.6% | 88.1% |
| Example 50 | LDL-TG sdLDL-C HDL-C ApoE ALT | 0.952 | 1.408 | 91.2% | 100.0% | 100.0% | 72.7% | 92.9% |
| Example 51 | LDL-TG HDL-C ApoB ApoE ALT | 0.949 | 1.866 | 88.2% | 100.0% | 100.0% | 66.7% | 90.5% |
| Example 52 | LDL-TG LDL-C HDL-C ApoE ALT | 0.938 | 1.383 | 91.2% | 87.5% | 96.9% | 70.0% | 90.5% |

TC: total cholesterol

As shown in Table 12, Examples 48 to 52 provided higher values of AUC and accuracy than those in Comparative Example 1 where only ALT, a conventional liver disease marker, was utilized, and those in Comparative Example 2 where only LDL-TG, another conventional liver disease marker, was utilized, as shown in Table 3-1, indicating that the development of NASH or NAFL could be predicted with a higher probability.

Examples 53 to 57

In Examples 53 to 57. the items shown in Table 13 were used, and binary variables created by dichotomizing each measured value at a cutoff value determined by the Youden's index for a ROC curve based on each single item were used as the amounts of the items. The values shown in Table 5 were used as the cutoff values of the respective items.

TABLE 13

| No. | Item |
|---|---|
| Example 53 | LDL-TG, sdLDL-C, HDL2-C, ApoE, ALT |
| Example 54 | LDL-TG, HDL-C, ApoE, TC |
| Example 55 | LDL-TG, sdLDL-C, HDL-C, ApoE, ALT |
| Example 56 | LDL-TG, HDL-C, ApoB, ApoE, ALT |
| Example 57 | LDL-TG, LDL-C, HDL-C, ApoE, ALT |

TC: total cholesterol

Mathematical models established by logistic regression analysis in the respective combinations are shown in Table 14. A score is calculated by substituting the value of each item for the variable represented by the name of the item in each mathematical model, where a value of 1 or 0 is substituted depending on whether the measured value of the item is larger or smaller than the cutoff value of the item.

TABLE 14

| No. | Mathematical model |
|---|---|
| Example 53 | +1.700 + 3.014LDL-TG − 3.423sdLDL-C − 2.927HDL2-C + 2.730ApoE − 0.779ALT |
| Example 54 | +31.556 + 2.766LDL-TG − 15.705HDL-C + 1.717ApoE − 17.414TC |
| Example 55 | +18.173 + 2.942LDL-TG − 2.558sdLDL-C − 17.418HDL-C + 1.700ApoE − 1.446ALT |
| Example 56 | +18.042 + 3.333LDL-TG − 17.296HDL-C − 2.175ApoB + 1.356ApoE − 1.280ALT |
| Example 57 | +17.192 + 3.464LDL-TG − 2.069LDL-C − 16.33HDL-C + 1.110ApoE − 1.306ALT |

TC: total cholesterol

The areas under ROC curves (AUC) for prediction of subjects positive for NASH, a deteiinined reference value, and the values of sensitivity, specificity, PPV (positive predictive value), NPV (negative predictive value), and accuracy determined by comparison between each reference value and each score are shown in Table 15.

TABLE 15

| No. | Item | AUC | Reference value | Sensitivity | Specificity | PPV | NPV | Accuracy |
|---|---|---|---|---|---|---|---|---|
| Example 53 | LDL-TG sdLDL-C HDL2-C ApoE ALT | 0.934 | 0.314 | 94.1% | 75.0% | 94.1% | 75.0% | 90.5% |
| Example 54 | LDL-TG HDL-C ApoE TC | 0.934 | 1.203 | 85.3% | 87.5% | 96.7% | 58.3% | 85.7% |
| Example 55 | LDL-TG sdLDL-C HDL-C ApoE ALT | 0.938 | 2.251 | 88.2% | 87.5% | 96.8% | 63.6% | 88.1% |
| Example 56 | LDL-TG HDL-C ApoB ApoE ALT | 0.936 | 0.624 | 94.1% | 75.0% | 94.1% | 75.0% | 90.5% |
| Example 57 | LDL-TG LDL-C HDL-C ApoE ALT | 0.904 | 0.862 | 94.1% | 75.0% | 94.1% | 75.0% | 90.5% |

TC: total cholesterol

As shown in Table 15, Examples 53 to 57 provided higher values of AUC and accuracy than those in Comparative Example 3 where only ALT, a conventional liver disease marker, was utilized, and those in Comparative Example 4 where only LDL-TG, another conventional liver disease marker, was utilized, as shown in Table 7-1, indicating that the development of NASH or NAFL could be predicted with a higher probability.

The invention claimed is:

1. A method of detecting LDL-TG and at least one component selected from the group consisting of LDL-C, LDL subfraction-C, HDL-C, HDL subfraction-C, ApoB, ApoE, total cholesterol, ALT, and AST, contained in a test blood sample isolated from a living body of a patient having nonalcoholic steatohepatitis, the method comprising:

a) measuring the amount of LDL-TG contained in the test blood sample;

b) measuring the amount of the at least one component in the test blood sample; and c) detecting whether at least one case of (1) to (3) below is satisfied:;

(1) the case in which a mathematical model with parameters which are the amount of LDL-TG and the amount of the at least one component is generated, the amount of LDL-TG and the amount of the at least one component contained in the test blood sample are substituted into the mathematical model to calculate a score, and the calculated score is larger than a reference value;

(2) the case in which the amount of LDL-TG is equal to or above the cutoff value of the LDL-TG and the amount of any test item selected from LDL-C, LDL subfraction-C, HDL-C, HDL subfraction-C, ApoB, total cholesterol, ALT, and AST is equal to or below the cutoff value of the test item;

(3) the case in which the amount of LDL-TG is equal to or above the cutoff value of the LDL-TG and the amount of ApoE is equal to or above the cutoff value of the ApoE.

2. The method according to claim 1, wherein the LDL subfraction-C is small dense (sd) LDL-C.

3. The method according to claim 1, wherein the HDL subfraction-C is ApoE containing HDL-C and/or HDL2-C and/or HDL3-C.

4. The method according to claim 1, further comprising generating a mathematical model with parameters which are the amount of LDL-TG and the amount of at least one component selected from the group consisting of LDL-C, LDL subfraction-C, HDL-C, HDL subfraction-C, ApoB, ApoE, total cholesterol, ALT, and AST, and substituting the amount of LDL-TG and the amount of the at least one component contained in the test blood sample into the mathematical model to calculate a score, wherein the possibility of having nonalcoholic steatohepatitis is determined to be high when the score is higher than that calculated from the amounts in blood samples from patients with nonalcoholic fatty liver.

5. The method according to claim 1, wherein the mathematical model is illustrated by the general formula (1) below:

$$\text{Score}=a+b\times[\text{the amount of LDL-TG}]+c\times[\text{the amount of LDL-C}]+d\times[\text{the amount of sdLDL-C}]+e\times[\text{the amount of ApoE-containing HDL-C}]+f\times[\text{the amount of HDL2-C}]+g\times[\text{the amount of HDL2-C}]+h\times[\text{the amount of HDL3-C}]+i\times[\text{the amount of ApoB}]+j\times[\text{the amount of ApoE}]+k\times[\text{the amount of total cholesterol}]+l\times[\text{the amount of ALT}]+m\times[\text{the amount of AST}] \quad (1)$$

US 12,571,806 B2

23 where in the formula (1), a represents an intercept, and b to m represent coefficients to respective measured values, where a to m may represent products of each number from a to m multiplied by the absolute value of itself, or where an arbitrary number may be added to or subtracted from the value of the intercept a;

in cases where continuous variables which are raw measured amount values are used as amounts for the above general formula (1), the intercept a is –10 to 10, the coefficient b is 0.1 to 1.5, the coefficient c is –1.0 to 0, the coefficient d is –1 to 0, the coefficient e is –1.0 to 0, the coefficient f is –2 to 0, the coefficient g is –1.0 to 0, the coefficient h is –1.0 to 0, the coefficient i is –1.0 to 0, the coefficient j is 0 to 10, the coefficient k is –1.0 to 0, the coefficient l is –1.0 to 0, the coefficient m is –1.0 to 0;

in cases where binary variables created by dichotomization at each given value are used as amounts for the above general formula (1), the intercept a is –100 to 100, the coefficient b is 1 to 10, the coefficient c is a number of –5.0 to 0, the coefficient d is a number of –5 to 0, the coefficient e is a number of –30 to 0, the coefficient f is a number of –30 to 0, the coefficient g is a number of –5 to 0, the coefficient h is a number of –30 to 0, the coefficient i is a number of –5 to 0, the coefficient j is a number of 0 to 10, the coefficient k is a number of –30 to 0, the coefficient l is a number of –5 to 0, the coefficient m is a number of –5 to 0.

6. The method according to claim 5, wherein
in cases where continuous variables which are raw measured amount values are used as amounts for the above general formula (1), the intercept a is –5 to 5, the coefficient b is 0.2 to 1.0, the coefficient c is –0.1 to 0, the coefficient d is –0.5 to 0, the coefficient e is –0.2 to 0, the coefficient f is –1.5 to 0, the coefficient g is –0.3 to 0, the coefficient h is –0.2 to 0, the coefficient i is –0.2 to 0, the coefficient j is 0 to 5, the coefficient k is –0.1 to 0, the coefficient l is –0.1 to 0, the coefficient m is –0.2 to 0;

in cases where binary variables created by dichotomization at each given value are used as amounts for the above general formula (1), the intercept a is 0 to 40, the coefficient b is 2 to 5, the coefficient c is a number of –3 to 0, the coefficient d is a number of –4 to 0, the coefficient e is a number of –20 to 0, the coefficient f is a number of –20 to 0, the coefficient g is a number of –3 to 0, the coefficient h is a number of –20 to 0, the coefficient i is a number of –3 to 0, the coefficient j is a number of 0 to 3, the coefficient k is a number of –20 to 0, the coefficient l is a number of –2 to 0, the coefficient m is a number of –2 to 0.

7. The method according to claim 1, wherein the reference value is set by using Youden's index.

8. The method according to claim 1, wherein the reference value is a score calculated from the amounts in blood samples from patients with nonalcoholic fatty liver.

* * * * *